United States Patent [19]

Klose et al.

[11] 4,268,628
[45] May 19, 1981

[54] METHOD FOR THE DETERMINATION OF α-AMYLASE

[75] Inventors: Sigmar Klose, Berg; Hans-Georg Batz, Tutzing; Michael Stoltz, Polling; Alexander Hagen; Günter Weimann, both of Tutzing, all of Fed. Rep. of Germany

[73] Assignee: Boehringer Mannheim GmbH, Mannheim-Waldhof, Fed. Rep. of Germany

[21] Appl. No.: 22,011

[22] Filed: Mar. 19, 1979

[30] Foreign Application Priority Data

Mar. 20, 1978 [DE] Fed. Rep. of Germany ....... 2812154

[51] Int. Cl.³ ............................................. C12Q 1/40
[52] U.S. Cl. ................................... 435/22; 435/805; 536/45
[58] Field of Search ............. 23/230 B; 106/213, 214; 210/22 C; 252/408 R; 435/22, 805; 536/45, 47, 50, 102, 105, 106, 111

[56] References Cited

U.S. PATENT DOCUMENTS

| | | | |
|---|---|---|---|
| 2,317,752 | 4/1943 | Fuller | 536/105 |
| 3,117,105 | 1/1964 | Borchert | 536/105 |
| 3,219,518 | 11/1965 | Barber et al. | 536/45 |
| 3,679,661 | 7/1972 | Babson | 435/22 |
| 3,694,318 | 9/1972 | Klein et al. | 435/22 |
| 3,888,739 | 6/1975 | Whetzel et al. | 435/22 |
| 4,025,392 | 5/1977 | Dougherty | 435/22 |
| 4,144,306 | 3/1979 | Figueras | 435/22 |

FOREIGN PATENT DOCUMENTS 50-57697  5/1975  Japan ..................................... 435/22

Primary Examiner—Peter A. Hruskoci
Attorney, Agent, or Firm—Sprung, Felfe, Horn, Lynch & Kramer

[57] ABSTRACT

Novel method for the determination of α-amylase which method comprises contacting a sample suspected of containing α-amylase with a starch derivative carrying a substituent capable of dyestuff-forming coupling; separating from the resulting starch-containing phase the low molecular weight soluble fission products formed by splitting of said starch derivative by α-amylase; coupling the said couplable substituent with another dyestuff forming component; and measuring the dyestuff so formed as a measure of the initial α-amylase content.

19 Claims, No Drawings

METHOD FOR THE DETERMINATION OF α-AMYLASE

The present invention is concerned with a process and reagent for the determination of α-amylase.

As is known, the enzyme α-amylase splits the α-1,4-glycosidic bond in polysaccharides, such as amylose, amylopectin and glycogen, as well as in their decomposition products with a chain length of at least 3 D-glucose residues, the reaction product being the disaccharide maltose. Maltose can be split, for example, by a α-glucosidase into glucose which, in turn, can be determined enzymatically. In this complex detection reaction, among other things, the glucose already present in a serum test sample has a disturbing effect.

In another known detection reaction for α-amylase, use is made of the known iodine starch reaction. In this case, the disappearance of the blue color of the iodine inclusion compound in the starch molecule is measured. Since this inclusion compound depends upon a helical chain structure of the starch, which is only partly present, this method of determination is relatively inexact (see published Federal Republic of Germany Patent Application Ser. No. 2,508,714).

On the other hand, great importance has been achieved by a determination process in which, from an insoluble starch colored with a dyestuff, by means of the action of α-amylase, soluble colored fragments are liberated which then colored the supernatant solution, the coloration of this solution being a measure for the amount of α-amylase present in the test sample. Besides the difficulty of preparing a reproducably equally strongly cross-linked, insoluble starch derivative, the dyestuff liberated in this method by hydrolysis also always has a disturbing effect, which gives rise to a certain blank value. The high molecular weight of the reactive dyestuff has an especially disturbing effect. The result of this is that, in the immediate neighborhood of the point of bonding to the sugar chain, an attack by the α-amylase cannot take place for steric reasons. The concentration of the dyestuff on the starch can, therefore, not be increased to any desired extent so that the measurable extinction is also limited. Since the molecular weight of the starch fragments is, in comparison with that of the dyestuff, relatively small, for example a separation of low molecular, colored fragments of colored soluble starch by dialysis is also not possible. However, just such a separation in a flowing solution system would be desirable for carrying out a determination in automatic analyzers.

The present invention substantially overcomes the disadvantages of the known methods for detecting α-amylase and provides a process for the determination of α-amylase which can be used in automatic analyzers with several separate solution cycles.

The present invention provides a process for the determination of α-amylase with the use of an oligomeric or polymeric starch derivative as substrate and specifically employs a starch derivative which carries a substituent capable of coupling with the formation of a dyestuff, the low molecular weight, soluble fission products formed by the splitting of the substrate by α-amylase being separated off from the starch-containing phase and coupled with a further dyestuff-forming component, whereafter the dyestuff so formed is measured.

An important feature of the present invention is the use of a starch derivative which is substituted with a low molecular weight compound capable of dyestuff formation instead of with a dyestuff. It is not necessary to employ a cross-linked, insoluble starch derivative; on the contrary, soluble starch as well as insoluble starch can be used.

The derivatization of the starch must be of such a nature that, upon splitting with α-amylase, a fragment is split off which can react with a further dyestuff-forming component to form a dyestuff. Since the starch derivative does not carry a voluminous dyestuff residue, attack by the α-amylase is also not hindered so that a very high degree of substitution can be chosen. The result of this is that the greater part of the resulting fission products carries a substituent capable of coupling with the formation of a dyestuff and, therefore, the determination has a high degree of sensitivity. Therefore, a starch derivative is preferably used which, for every 6 to 30 glucose units, has a substituent capable of coupling with the formation of dyestuff. However, it is also possible to employ starch derivatives with a still higher degree of substitution. On the other hand, under certain circumstances, it can also suffice when there is only one substituent capable of coupling for more than 30 glucose units if high sensitivity is not required. A starch derivative which carries one substituent capable of coupling for every 15 to 25 glucose units has proved to be especially useful in automatic analyzers.

In principle, all components capable of dyestuff formation can be used as substituents for the starch, provided that they do not have a high molecular weight, give soluble fission products in the case of the action of the α-amylase and can be reacted to give a readily measurable dyestuff. Those substituents are preferred which are so small that the fragment split off by the fission of the substrate is dialysable. Appropriate dyestuff-forming components are well known, as are the reactions and coupling components leading to dyestuff formation. However, the substituent must not contain any functions which impair the enzymatic activity of the α-amylase.

According to the present invention, starch derivatives have proved to be especially useful which are substituted with a compound of the general formula:

(I)

wherein R is a hydrogen atom or an alkyl radical containing up to 4 carbon atoms or an —(CH$_2$)$_n$—X radical, X is a function capable of forming a covalent bond with a hydroxyl group of the starch and n is 1, 2, 3 or 4.

Another preferred group of starch derivatives are those which are substituted by a compound of the general formula:

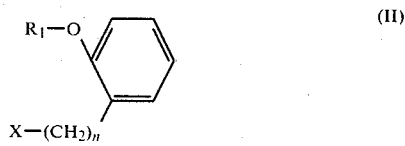

(II)

wherein $R_1$ is a hydrogen atom or a protective group which is easily split off, such as an acyl radical, and X and n have the same meanings as in general formula (I).

A further preferred group of starch derivatives corresponds to the general formula:

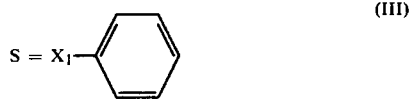 (III)

wherein $X_1$ is —N— or

and S is a starch residue.

Functions capable of forming a covalent bond with a hydroxyl group of the starch which have proved to be especially useful include oxirane groups, halogen atoms, acid chloride group, isocyanate groups, isothiocyanate groups, tosylate groups, dichlorotriazine groups or mesylate groups. However, this list is not exhaustive and numerous other groups capable of reaction with a hydroxyl group of starch are well known.

The further component capable of coupling with the substituents of general formulae (I) and (II), with the formation of dyestuff, is preferably a diazonium salt or a compound capable of oxidative coupling with phenols or anilines. Especially suitable within this preferred group are N-alkylpyridone-(4)-hydrazone derivatives, especially N-methylbenzthiazolone-hydrazone, aminodimethylaniline and 1-phenyl-2,3-dimethyl-4-amino-3-pyrazolin-5-one (4-aminophenazone). For the oxidative coupling, it is especially preferred to use ferric chloride, potassium ferricyanide, copper sulphate, silver nitrate, sodium hypochloride, lead dioxide, ceric sulphate, hydrogen peroxide or, in general, hydrogen peroxide-forming reaction systems.

A preferred compound of general formula (I) is N-methyl-N-(2,3-epoxypropyl)-aniline: when oxidatively coupled with N-methylbenzthiazolone-hydrazone (MBTH), a dyestuff is obtained with a very high extinction maximum at the wavelengths 570 to 600 mμ, which is especially well suited for measurement.

For the reaction with an aniline or phenyl-hydrazine derivative, it is preferble to use a starch in which every 10th to 50th glucose unit has been oxidized.

The separation of the low molecular weight soluble fission products formed by splitting the substrate can take place, for example, by dialysis, filtration or centrifuging, these methods being especially useful when using an insoluble starch derivative. However, when using soluble starch derivatives, dialysis or ultrafiltration is preferably employed for the separation. In the case of soluble starch derivatives, the low molecular weight fission products are preferably separated by dialysis, a proportion of the fission products being dialysed out from a first continuous liquid stream into a second liquid stream which is passed along on the other side of the dialysis membrane. The dialysis membrane used for this purpose is preferably one with a high permeability, not only with regard to the quality but also to molecule size.

As already mentioned above, the process according to the present invention is well suited for use in conventional autimtic analyzers and especially in those in which several separate solution cycles are present, which are connected with one another by a dialysis membrane. The primary cycle then contains the solution or insoluble starch derivatives. The low molecular weight, soluble fission product with the substituent capable of dyestuff formation passes through the dialysis membrane into the secondary cycle and is there reacted to give a dyestuff, the latter being measured. The dyestuff is usually measured with a photometer which measures in the visible range or possibly also in UV.

The starch derivative employed according to the present invention is, in general, used in an amount of from 0.05 to 3% by weight and preferably of from 0.5 to 2% by weight. The action of the α-amylase takes place at a pH value of from 5.0 to 9.0 and preferably of from 6.5 to 7.5. For the activation of the amylase, it is preferable to add chloride ions, for example in the form of sodium or potassium chloride, in amounts of from 0.01 to 12% and preferably of from 0.05 to 5%. The incubation time depends upon the temperature and the degree of substitution of the starch derivative employed: in the case of an incubation temperature of 45° C., an incubation time of from 3 to 12 minutes generally suffices.

The present invention also provides a reagent for the determination of α-amylase which, as an essential component, contains a starch derivative carrying a substituent capable of coupling with dyestuff formation.

In a preferred embodiment, the reagent according to the present invention contains a starch derivative of the general formula:

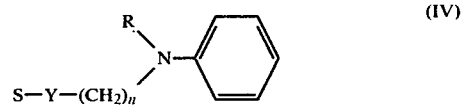 (IV)

wherein R is a hydrogen atom or an alkyl radical containing up to 4 carbon atoms or a —$(CH_2)_n$—Y—S radical, Y is the residue of a function reactive with hydroxyl groups, S the residue of starch and n is 1, 2, 3 or 4.

In a preferred embodimental form, the reagent contains a starch derivative of the general formula:

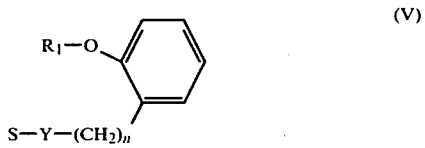 (V)

wherein $R_1$ is a hydrogen atom or a protective group which is easily split off, such as an acyl radical, and S, Y and n have the same meanings as in general formula (IV).

The reagent according to the present invention preferably contains, separate from the starch derivative, a dyestuff-forming component which can react with the substituent of the starch derivative with dyestuff formation. It is preferably a diazonium salt or a compound capable of oxidative coupling with phenols or anilines, together with an oxidation agent. Compounds which can be used for the oxidative coupling are preferably N-alkylpyridone-(4)-hydrazone derivatives, such as N-methylbenzthiazolone-hydrazone, aminodimethylaniline or 4-aminophenazone.

Furthermore, the reagent according to the present invention preferably also contains a buffer and chloride ions.

The reagent according to the present invention can be impregnated into an absorbent carrier, which can be in the form of a leaf or rodlet. In these cases, it is also possible to bond the modified starch covalently with the carrier material, for example filter paper. Such a bonding can be carried out with the use of hydroxy reagents, such as mentioned above, for example by means of epichlorohydrin.

The test strips are dipped into the solution to be investigated and, after a certain reaction time, again taken out. The color coupling reaction can subsequently be carried out either in the solution which contains the derivatized fragments or on the test strip itself, in which case coupling takes place with the dyestuff-forming substituents which have not been split off.

The following Examples are given for the purpose of illustrating the present invention:

EXAMPLE 1

A. Preparation of a derivatised starch 100 g. Zulkowski starch (see K. Zulkowski, Ber., 13, 1395/1800) are dissolved in a solution of 600 ml. water and 20 g. sodium hydroxide. To this solution are added 10 ml. N-methyl-N-(2,3-epoxypropyl-aniline (prepared as described in J. Chem. Soc., 1950, 890 et seq.), the resultant emulsion being stirred for 5 days at ambient temperature. The product is subsequently precipitated out by adding dropwise to a 4 fold amount of methanol and then filtered off with suction and dried. Yield 95%. Nitrogen content 0.46%, corresponding to one aniline group per 18 glucose units.

B. Oxidative coupling with MBTH

A 0.5% aqueous solution of the Zyulkowski starch according to A derivatized with epoxypropyl-N-methylaniline in 0.1 mol/liter phosphate buffer (pH 7.0) containing 5% sodium chloride is sucked, with the use of a peristaltic pump, through a tube at a flow rate of 1.0 ml./min. After air segmentation of this stream of liquid, at a flow rate of 0.1 ml./min., it is dosed with a serum sample containing α-amylase. This air-segmented stream of liquid is, after an incubation time of 7 minutes at 45° C., passed along above a dialysis membrane. The aniline-starch fragments split off by the α-amylase dialyse in a percentage amount which remains constant over the range in question. On the opposite side of the dialysis membrane flows surfactant-containing water ("Brij" 35) at a flow rate of 1 ml./min. ("Brij" is a Registered Trade Mark). Into this stream of liquid, enriched by the dialysate, which is also air segmented, there is dosed a 0.5% aqueous solution of methylbenzthiazolone-hydrazone (MBTH) at a rate of 0.1 ml./min. and, after mixing in a mixing coil, there is added thereto a 1% aqueous solution of potassium ferricyanide at a rate of 0.23 ml./min. The extinction of the resulting violet dyestuff is measured in a flow-through cuvette in a photometer at 560 nm and recorded. By comparison with the extinction of a sample with a known concentration of α-amylase, there is determined the α-amylase concentration in the test sample

EXAMPLE 2

A. Coupling of aniline via Schiff's base on to oxidized starch 6.6 g. Sodium periodate are added to a solution of 100 g. Zulkowski starch in 1.3 liter water. The mixture is stirred overnight, whereafter the oxidized starch solution is precipitated out by adding dropwise to 4 liter methanol.

50 g. of the oxidized starch are dissolved in 600 ml. water and then 350 ml. 15% acetic acid are added thereto, whereafter 50 ml. aniline are slowly added dropwise to this solution, with stirring. After a reaction time of 20 hours, the product is precipitated out by adding dropwise to a 3 fold amount of methanol and then filtered off with suction, washed with diethyl ether and dried.

B. Oxidative coupling with 4-aminophenazone

The procedure described in Example 1 is repeated but the use of the starch derivative of Example 2 A obtained by oxidation and coupling with aniline. Instead of MBTH, 4-aminophenazone is used, ferric chloride serving as the oxidation agent. Evaluation is carried out as described in Example 1.

EXAMPLE 3

A. Preparation of a starch derivative 100 g. Insoluble starch are suspended in a solution of 150 ml. water and 20 g. sodium hydroxide. 10 ml Ortho-2,3-epoxypropylphenol (prepared as described in J. Org. Chem., 24, 1197/1959) are then added thereto and the mixture obtained is stirred for 5 days at ambient temperature. The product is filtered off, washed with water and dried.

B. Oxidative coupling with 4-aminophenazone 0.1 ml. of an α-amylase-containing sample are added to a suspension of 10 mg. of the substrate prepared according to Example 3 A in 10 ml. phosphate buffer (20 mMol/l.) (pH 7.0), with the addition of 50 mMol/l. sodium chloride. The mixture is incubated for 15 minutes at 30° C. Subsequently, the proportion of the substrate which has not gone into solution is centrifuged off. To the supernatant is added 0.1 ml. of a 0.5% aqueous solution of 4-aminophenazone, as well as 0.1 ml. of a 1% solution of potassium ferricyanide. The extinction of the resulting dyestuff is measured at 578 nm.

EXAMPLE 4

POD-catalyzed oxidative coupling

A 2% aqueous solution of the Zulkowski starch of Example 1 derivatized with N-epoxypropyl-N-methylaniline in 0.1 mol/l. phosphate buffer (pH 7.0), containing 0.06% sodium chloride and 2 U glucose oxidase (GOD)/ml is, with the help of a peristaltic pump, sucked through a tube at a flow rate of 0.8 ml./min. After air-segmentation of this stream of liquid, a urine sample is dosed in at a flow rate of 0.1 ml./min., as well as an aqueous glucose solution with a concentration of 200 mg./100 ml. at a flow rate of 0.1 ml./min. This stream of liquid is, after incubating for 7 minutes at 45° C., passed along above a dialysis membrane. The aniline-starch fragments split off by the α-amylase and the hydrogen peroxide resulting by the GOD reaction migrate through the membrane, on the other side of which flows a surfactant-containing water at a flow rate of 0.6 ml./min. To this dialysate-enriched stream of liquid, which is also air-segmented, there is added a 0.05% aqueous solution of MBTH and 5 U peroxidase (POD)/ml. in 0.1 mol/liter citric acid/citrate buffer (pH 4.0) at a flow rate of 0.42 ml./min. After mixing in a mixing coil, the stream of liquid is passed through a flow-through cuvette in a photometer. The extinction of the resultant dyestuff is measured at 560 nm and recorded. By comparison with the extinction of a sample with a known concentration of α-amylase, there is determined the α-amylase concentration in the test sample.

EXAMPLE 5

Diazo coupling with echtrot salt

The experimental arrangement of Example 1 is used. However, in the secondary cycle, the solution taken up is carried out at a flow rate of 0.6 ml./min. of surfactant-containing water. Instead of MBTH, there is added thereto a 0.6% solution of echtrot salt in 0.025N sulphuric acid at a flow rate of 0.4 ml./min. The measurement of the extinction is carried out at 505 nm.

EXAMPLE 6

Preparation of a test strip

Filter paper is cut up into strips and dipped into a solution of epichlorohydrin in acetone. After 1 hour, the strips are taken out and coated with a starch derivatized in the manner described in Example 1 A. The coated, modified filter paper thus obtained is treated with warm 2N aqueous solution of sodium hydroxide, a covalent bonding between the paper and the starch hereby taking place. The strip so obtained is then washed with water and dried.

It will be understood that the specification and examples are illustrative but not limitative of the present invention and that other embodiments within the spirit and scope of the invention will suggest themselves to those skilled in the art.

What is claimed is:

1. Method for the determination of alpha-amylase which method comprises contacting at a pH of from 5 to 9, a sample suspected of containing alpha-amylase with a starch derivative carrying couplable substituents capable of dyestuff-forming coupling, to split said starch derivative by said alpha-amylase, forming a starch-containing phase and low molecular weight soluble fission products containing said couplable substituents;

separating from the resulting said starch-containing phase the low molecular weight soluble fission products, coupling said couplable substituents with a dyestuff-forming component, and measuring the dyestuff so formed as a measure of the initial alpha-amylase content;

wherein said starch derivative is substituted with a compound of the formula

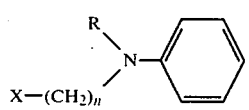

wherein

R is a hydrogen atom or an alkyl radical containing up to 4 carbon atoms or an $-(CH_2)_n-X$ radical, X is a function capable of forming covalent bond with a hydroxyl group of the starch, and n is 1, 2, 3 or 4 or with a compound of the formula

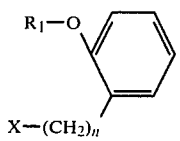

wherein $R_1$ is a hydrogen atom or a protective group which is easily split off, and X and n have the same meanings as in formula (I) or wherein the starch derivative is of the formula

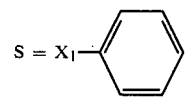

wherein $X_1$ -N- or

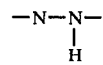

and S is a starch residue.

2. Method as claimed in claim 1 wherein said starch derivative contains said couplable substituents capable of dyestuff-forming coupling in an amount of one substituent per 6 to 30 glucose units in said starch derivative.

3. Method as claimed in claim 2 wherein said starch derivative contains said couplable substituents capable of dyestuff-forming coupling in an amount of one substituent per 15 to 25 glucose units in said starch derivative.

4. Method as claimed in claim 1 wherein said starch derivative is substituted with a compound of the formula

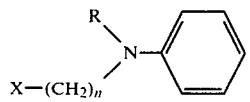

wherein

R is a hydrogen atom or an alkyl radical containing up to 4 carbon atoms or a $-X-(CH_2)_n$ radical, X is a function capable of forming covalent bond with a hydroxyl group of the starch and n is 1, 2, 3, or 4.

5. Method as claimed in claim 4 wherein

X is an oxirane group, a halogen atom, an acid chloride group, an isocyanate group, an isothiocyanate group, a tosylate group, a dichlorotriazine group or a mesylate group.

6. Method as claimed in claim 4 wherein a diazonium salt is used as the dyestuff-forming component.

7. Method as claimed in claim 4 wherein a compound capable of oxidative coupling with a phenol or aniline is used as the dyestuff-forming component.

8. Method as claimed in claim 7 wherein said dyestuff forming component is selected from N-alkylpyridone-(4)-hydrazone derivative, aminodimethyl-aniline and 1-phenyl-2,3-dimethyl-4-amino-3-pyrazolin-5-one.

9. Method as claimed in claim 8 wherein the N-alkyl-pyridone-(4)-hydrazone derivative used is N-methyl-benzthiazolone-hydrazone.

10. Method as claimed in claim 7 wherein the oxidative coupling is carried out with ferric chloride, potassium ferricyanide, copper sulphate, silver nitrate, sodium hypochlorite, lead dioxide, ceric sulphate, hydrogen peroxide or a hydrogen peroxide-forming reaction.

11. Method as claimed in claim 1 wherein the starch employed has been reacted with a compound of the formula

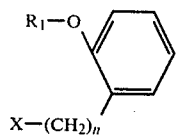

wherein $R_1$ is a hydrogen atom or a protective group which is easily split off and X is a function capable of forming covalent bond with a hydroxyl group of the starch and n is 1, 2, 3, or 4.

12. Method as claimed in claim 11 wherein the protective group $R_1$ is an acyl radical.

13. Method as claimed in claim 1 wherein said starch derivative is one in which every 10th to 50th glucose unit has been oxidized is reacted with an aniline derivative to give a Schiff base or with a phenyl-hydrazine derivative to give a hydrazone.

14. Method as claimed in claim 13, wherein the resulting Schiff base or hydrazone is reduced to give the corresponding amine.

15. Method as claimed in claim 1 wherein the low molecular weight, soluble fission product is separated by dialysis, filtration or centrifugation.

16. Method as claimed in claim 15 wherein in the case of a soluble starch derivative, the low molecular weight, soluble fission products are separated off by dialysis, a proportion of the fission products being dialysed from a first continuous stream of liquid into a second stream of liquid which is passed along on the other side of the dialysis membrane.

17. Method as claimed in claim 16 wherein a dialysis membrane with high permeability is used.

18. Method as claimed in claim 1 wherein said starch derivative is provided absorbed into an absorbent carrier.

19. Method as claimed in claim 18 wherein said carrier is in the form of test paper or rodlet.

* * * * *